United States Patent [19]
Ripley et al.

[11] Patent Number: 5,271,411
[45] Date of Patent: Dec. 21, 1993

[54] METHOD AND APPARATUS FOR ECG SIGNAL ANALYSIS AND CARDIAC ARRHYTHMIA DETECTION

[75] Inventors: Kenneth L. Ripley, Chesterfield, Mo.; Daniel T. Kaplan, Montreal, Canada

[73] Assignee: Colin Electronics Co., Ltd., Aichi, Japan

[21] Appl. No.: 757,307

[22] Filed: Sep. 10, 1991

Related U.S. Application Data

[63] Continuation-in-part of Ser. No. 586,492, Sep. 21, 1990, abandoned.

[51] Int. Cl.⁵ .................................... A61B 5/0472
[52] U.S. Cl. .................... 128/702; 364/413.06
[58] Field of Search .......... 128/702, 696, 703; 364/413.06

[56] References Cited

U.S. PATENT DOCUMENTS

| | | |
|---|---|---|
| 3,940,692 | 2/1976 | Neilson . |
| 4,046,504 | 10/1991 | Albert et al. . |
| 4,090,505 | 5/1978 | Mortara . |
| 4,170,992 | 10/1979 | Dillman . |
| 4,316,249 | 2/1982 | Gallant et al. . |
| 4,336,810 | 6/1982 | Anderson et al. . |
| 4,422,459 | 9/1991 | Simson . |
| 4,583,553 | 4/1986 | Shah et al. . |
| 4,589,420 | 5/1986 | Adams et al. . |
| 4,732,158 | 3/1988 | Sadeh . |
| 4,742,458 | 5/1988 | Nathans et al. . |
| 4,784,153 | 11/1988 | Marks . |
| 4,924,875 | 5/1990 | Chamoun . |
| 4,974,162 | 11/1990 | Seigel et al. . |

OTHER PUBLICATIONS

"Introduction To Automated Arrhythmia Detection"; K. Ripley And A. Murray; IEEE Computer Society; Computer Society Press; 1980; pp. 1-335.

"Biomedical Instrumentation and Measurements"; L. Cronwell et al; Prentice-Hall, Inc., New Jersey; 1980; pp. 55-57, 105-126; 413-417.

"Principles Of Applied Biomedical Instrumentation"; Geddes et al.; John Wiley & Sons, Inc.,; 1975; pp. 447-477.

Primary Examiner—William E. Kamm
Assistant Examiner—Kennedy J. Schaetzle
Attorney, Agent, or Firm—Oliff & Berridge

[57] ABSTRACT

A method and apparatus for arrhythmia detection comprise steps and means for acquiring at least one continuous analog signal produced by an ECG system, producing at least one digital signal based on the analog signal, producing a plurality of scalar signals from the at least one digital signal, extracting features from the scalar signal, and plotting the extracted features in a feature space having a number of dimensions equal to the number of extracted features. A normal QRS complex is identified based on the population of QRS complexes located within clusters of QRS features within the feature space. Subsequent QRS complexes acquired after identification of the normal QRS complex are labeled based on a plurality of rules and the location of each subsequent QRS complex with respect to both prior and subsequent normal QRS complexes.

39 Claims, 7 Drawing Sheets

Fa

Fb

Fc

Fd ized and filtered by hardware circuitry and then
METHOD AND APPARATUS FOR ECG SIGNAL ANALYSIS AND CARDIAC ARRHYTHMIA DETECTION This is a continuation-in-part of application Ser. No. 07/586,492, filed Sep. 21, 1990, now abandoned.

FIELD OF THE INVENTION

The present invention relates generally to an electrocardiogram (ECG) system, and, more specifically, to a method and an apparatus for detecting arrhythmia based on the features of QRS complexes within a signal produced by the cardiovascular system of a subject.

BACKGROUND OF THE INVENTION

FIG. 1 shows a section of a typical ECG waveform containing two normal beats and one abnormal beat. Methods and apparatus are known for the quantification of QRS morphology in ECG signals using a small set of numbers or features to aid in detecting, for example, premature ventricular contractions (PVCs) and in quantifying cardiac arrhythmias. In general, morphology information is used to group heart beats into similar classes, so that information from morphologically similar beats can be used to assist in judging whether a given beat is normal or abnormal, e.g., a PVC.

In a conventional QRS feature extraction system, the first step is QRS detection. Once a putative QRS is detected, a segment of the ECG data is pulled out in a window surrounding the time of detection. The ECG data in the window, e.g., a QRS pattern vector, is then transformed into features which describe QRS morphology, e.g., the QRS feature vector.

A number of techniques for translating the QRS pattern vector into a small number of features have been proposed and implemented. U.S. Pat. No. 4,336,810, for example, discloses a method and apparatus for arrhythmia analysis of ECG recordings wherein a magnetically recorded ECG tape is scanned for QRS complexes. The scanned ECG signal is converted into a digital representation and then compared to previously known QRS patterns which are grouped together as templates. If no match is found for the current QRS complex, a new template is created and the next QRS complex is scanned and classified. To classify each QRS complex, characteristics of a QRS complex's shape are used, which include the width of the complex and the area above and below the baseline of the QRS complex. Once each QRS complex is classified using the templates, the complexes are labeled as normal, supraventricular ectopic, ventricular ectopic or unknown. U.S. Pat. No. 4,583,553 discloses an ambulatory ECG analyzer and recorder wherein a patient's ECG signal is digitized and filtered by hardware circuitry and then used as an input for algorithm, which detects a QRS complex, classifies it, groups it into a collection of like complexes and generates a report based on its findings. An algorithm, which is designed to work in real time, detects up to 43 events, but prioritizes the events based on a particular patient. The algorithm uses a two channel ECG to minimize classification errors.

U.S. Pat. No. 4,742,458 discloses a method and apparatus for performing pattern recognition analysis wherein an ECG signal is filtered to allow hardware circuitry to analyze a QRS complex within an ECG signal. Two features of the QRS complex, which include slope transitions and intervals between slope transitions, are used to create a signature for the ECG signal. Once a QRS complex is captured and classified, it is grouped into a classification of like complexes or, if no match is found, a new classification is created.

U.S. Pat. No. 4,589,420 discloses a method and apparatus for ECG rhythm analysis using an algorithm which detects a QRS complex within an ECG signal, classifies it and uses it to determine characteristics about a patient's condition. A number of different characteristics of a QRS complex are extracted from the ECG signal, including QRS complex width, R-R interval and instantaneous and averaged heart rates. A determination and classification of the complex is made based on the amount of noise present within the complex. Beats are classified using a two step process wherein each new QRS complex is tested against previous complexes and then by a finite state machine process based on the results of the previous complex matching step.

SUMMARY OF THE INVENTION

Accordingly, the principal object of the present invention is to provide a method and an apparatus for labeling QRS complexes so as to distinguish between normal and abnormal QRS complexes.

Another object of the present invention is to provide a method of identifying a normal QRS complex based on N features of possible QRS complexes plotted within an N-dimensional feature space.

A further object of the present invention is to provide an apparatus for distinguishing between normal and abnormal QRS complexes provided by the ECG system based on clusters of QRS complexes within a feature space.

A still further object of the present invention is to provide a method of labeling QRS complexes as normal or abnormal based on the population of QRS complexes within clusters located within a feature space.

Another object of the present invention is to provide a method for locating QRS complexes which is insensitive to noise and baseline drift.

These and other objects and advantages are achieved in accordance with the present invention by acquiring at least one continuous analog signal produced by an ECG system, producing at least one digital signal based on the analog signal, producing a plurality of scalar signals from the at least one digital signal, extracting features from the scalar signal, and plotting the extracted features in a feature space having a number of dimensions equal to the number of extracted features. A normal QRS complex is identified based on the population and timing of QRS complexes located within clusters of QRS features within the feature space. Subsequent QRS complexes acquired after identification of the normal QRS complex are labeled based in part on the location of each subsequent QRS complex with respect to the normal QRS complex.

These and other objects and advantages are achieved in accordance with the present invention by a method comprising the steps of extracting a number N of features based on the time of occurrence of a plurality of possible first QRS complexes within a digital signal, plotting N features in an N-dimensional feature space so as to produce a plurality of clusters of the features, identifying a normal QRS complex type based on the clusters, labeling a plurality of second QRS complexes within the digital signal based on the N features of each of the second QRS complexes and the normal QRS complex, and displaying the labeled QRS complexes.

According to a first embodiment of the method of the claimed invention, the time of occurrence of the QRS complexes is determined by the steps of locating the time at which the scalar signal crosses predetermined threshold and then locating a local maximum of the scalar signal. According to a second preferred embodiment of the method of the claimed invention, the time of occurrence is determined by the steps of receiving as input to a plurality of basis filters the digital signal vectors, combining the outputs of the basis filters and locating a local maximum of the combined output of the basis filters.

These and other objects and advantages are achieved in accordance with the present invention by an arrhythmia detection system comprising receiving means for receiving at least one analog ECG signal at a predetermined sampling frequency, converting means for producing at least one digital signal from the at least one analog ECG signal, processing means for producing diagnostic information, the processing means comprising first means for identifying a normal QRS complex based on a plurality of first QRS complexes, second means for labeling each QRS complex within a plurality of second QRS complexes based on the normal QRS complex, and display means for displaying the labeled QRS complexes.

These and other objects and advantages of the present invention are achieved by a method of QRS complex and feature extraction comprising the steps of receiving at least one digital signal, applying the at least one digital signal to a plurality of filters so as to produce a plurality of features, producing a combined feature based on the features, determining a plurality of times of occurrence based on the combined feature, and locating a plurality of QRS complexes corresponding to the times of occurrence.

These and other objects, features and advantages of the invention are disclosed in or apparent from the following description of preferred embodiments.

BRIEF DESCRIPTION OF THE DRAWINGS

The preferred embodiments are described with reference to the drawings, in which like elements are generally denoted by like numbers, and in which.

DESCRIPTION OF THE PREFERRED EMBODIMENTS

Figure 1:
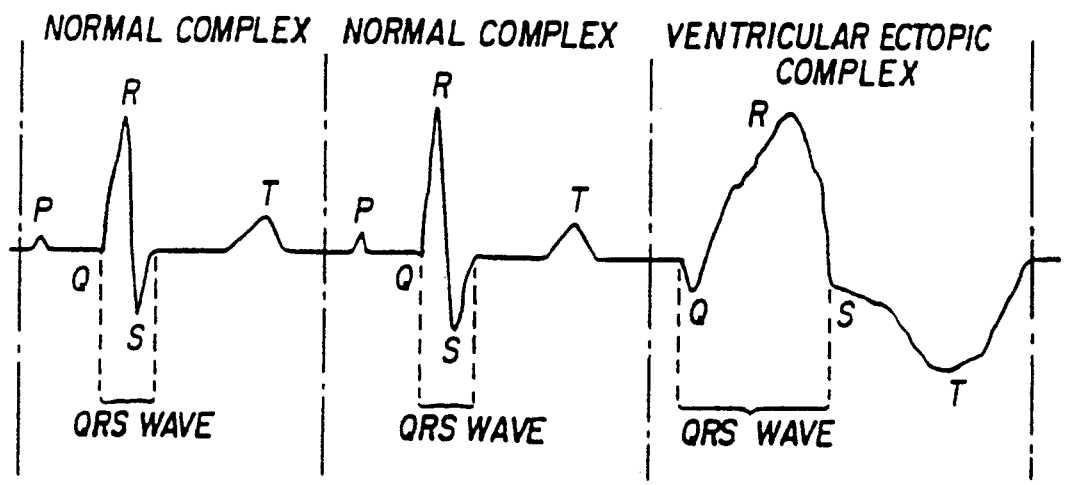
FIG. 1 shows a section of a typical ECG waveform.
Figure 2:
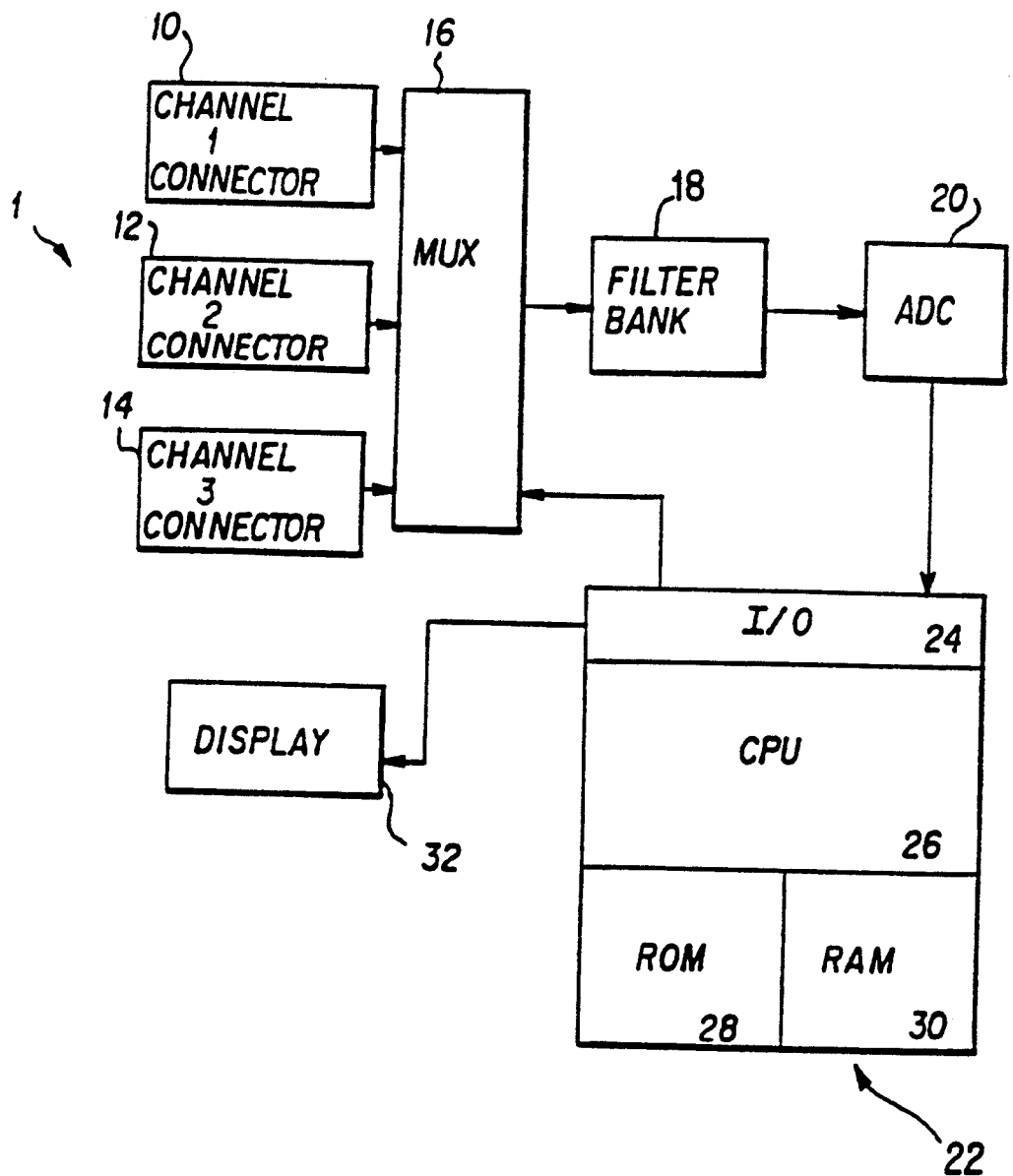
FIG. 2 shows a schematic diagram of an arrhythmia detection system according to the present invention.

Referring to FIG. 2, an arrhythmia detection system 1 according to the present invention comprises a first channel connector 10, a second channel connector 12 and a third channel connector 14, which are connected to a conventional ECG system for receiving ECG signals, an analog-to-digital converter (ADC) circuit 20 for receiving ECG signals via multiplexing circuitry (MUX) 16 and filter bank 18 for converting ECG signals to digital signals, a microprocessor 22 for manipulating and quantifying the digital signals, and a display 32 for displaying annotated ECG data. Microprocessor 22 advantageously comprises an input-output (I/O) circuit 24 for receiving digital signals and transferring output ECG data, a central processing unit (CPU) 26, a read only memory (ROM) 28 for storing program instructions and fixed constants and a random access memory (RAM) 30 for storing digital signals, intermediate program results and variable constants.

I/O 24 advantageously provides a timing signal T to MUX 16 for controlling the timing of ECG signal collection. Preferably, signal T provides for sampling each channel connector 10, 12 and 14 at a frequency of about 250 Hertz (Hz). The sampling frequency produced by signal T advantageously can be set at 300 Hz so as to cooperate with anti-aliasing filters in filter bank 18, which are discussed below. Preferably, ADC 20 is a conventional ADC circuit providing at least 12 bits of data with a resolution of less than 2.4 microvolts per unit of resolution and having a nominal operating voltage of ±5.0 volts.

Filter bank 18 advantageously comprises a conventional low pass anti-aliasing filter for removing high frequency noise from received ECG signals. Filter bank 18 advantageously can contain conventional notch stop filters for removing extraneous AC line frequency and harmonic noise from received ECG signals. It will be appreciated that the AC line frequency notch filters can also be implemented in software by microprocessor 22.

Preferably, display 32 is a conventional strip chart recorder for displaying ECG data, i.e., annotated ECG waveforms. It will be appreciated that microprocessor 22 and display 32 can cooperate to provide a tabular representation of ECG data.

System 1 is shown in FIG. 2 comprising collectors 10, 12 and 14, which provides means for receiving three analog ECG signals simultaneously. Preferably, system 1 receives three ECG signals from a conventional ECG system (not shown). Microprocessor 22 advantageously can be used to provide one or two signals if three ECG signals are not available from the ECG system. If two ECG signals are available, microprocessor 22 provides an interpolated ECG signal based on the difference between the two available ECG signals. If only one ECG signal is available, microprocessor 22 provides a first extrapolated signal equal to 0.5 times the available ECG signal, and a second extrapolated ECG signal equal to $-1.0$ times the available ECG signal.

Figure 3:
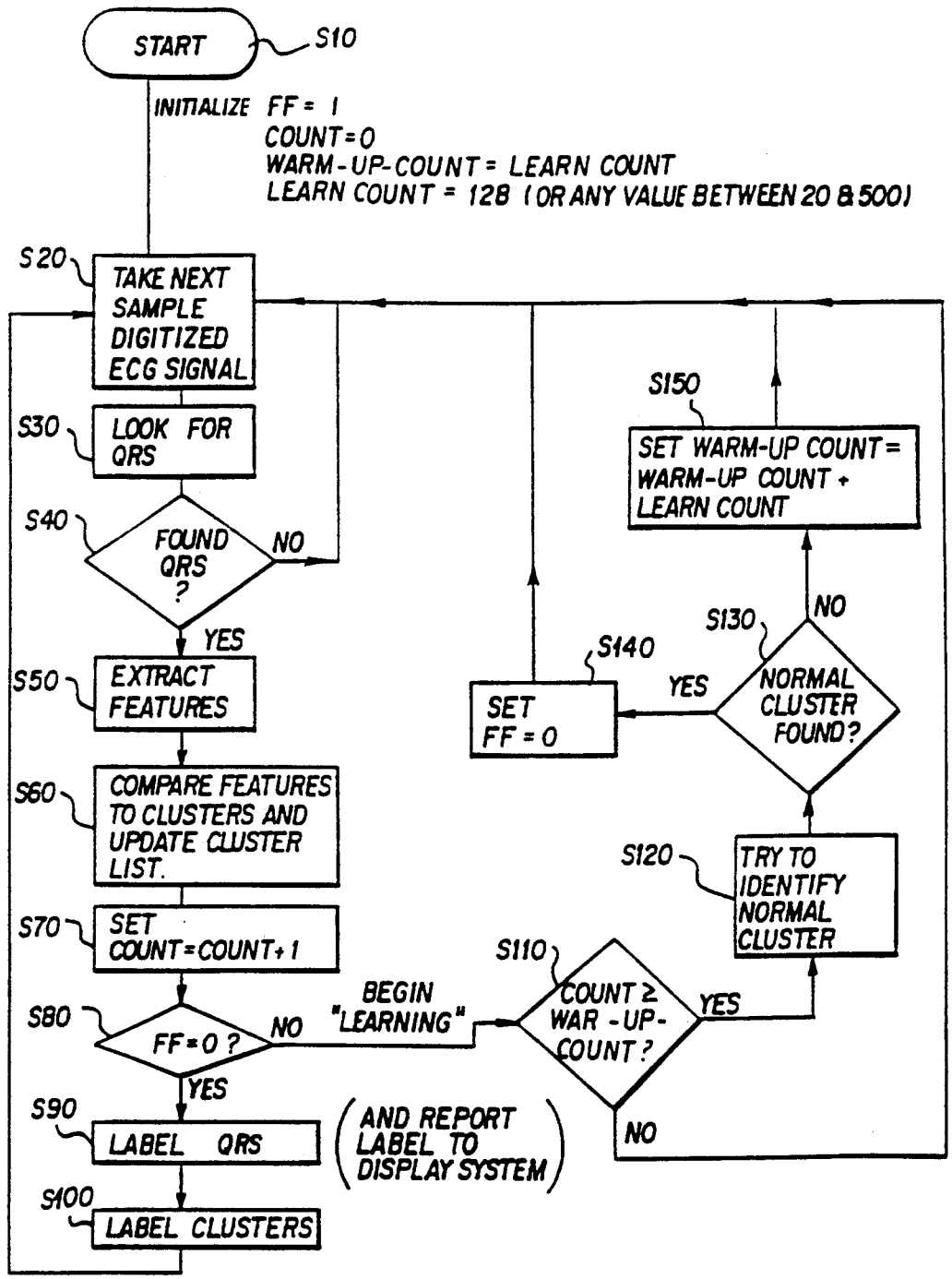
FIG. 3 shows a high level flow chart of the operational steps implemented by the system shown in FIG. 2 for classifying QRS complexes according to the present invention.

The operation of arrhythmia detection system 1 according to a first embodiment of the present invention is explained while referring to FIGS. 2 through 4.

Referring to FIG. 3, at step S10 system 1 start up occurs, during which system 1 is initialized. Initialization includes clearing the feature space and setting a value COUNT equal to zero. In addition, a flag FF is set equal to 1 to indicate an initializing state and value WARM_UP_COUNT is set equal to a predetermined value LEARNCOUNT. Preferably, LEARNCOUNT is equal to about 128, although LEARNCOUNT advantageously can be any value within a range of about 20 to 500.

At step S20, ECG signals are received. Collector 10, 12 and 14, MUX 16, filter bank 18 and ADC advantageously cooperate to acquire analog ECG signals, convert the analog signals to digital signals, and store the digital signals in RAM 30. MUX 16 and I/O 24 further cooperate to sample the ECG signals at a predetermined sampling frequency, i.e., about 250 Hz or about 300 Hz. Thus, the digital signals, preferably in vector form $e_1(t)$, $e_2(t)$, $e_3(t)$, corresponding to ECG signals received via collectors 10, 12 and 14, respectively, are acquired and stored in RAM 30.

Figure 4A:
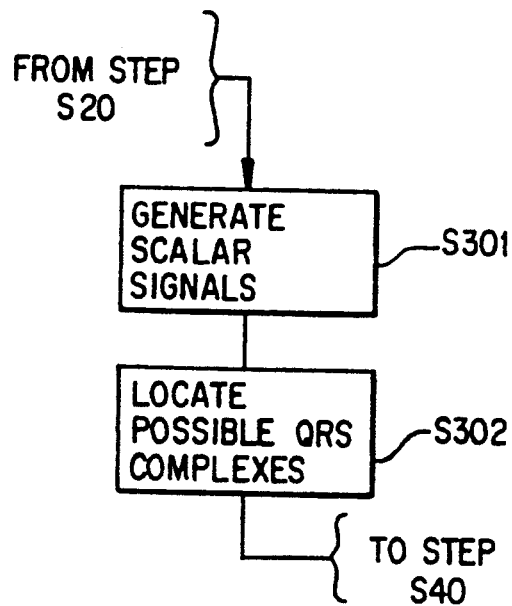
FIGS. 4A and 4B show low level flow charts of the operational steps implemented by steps S30 and S50 of FIG. 3 according to a first preferred embodiment of the present invention.

During step S30, the program checks to see if a possible QRS complex has been located within the digital signals. Referring to FIG. 4A, the detailed steps of the QRS complex location routine are shown starting at step 301, in which digital signal vectors are converted to scalar signals. Scalar signals are formed using the formulae:

$$m(t) = |[e_1(t) - e_1(t-1)][e_2(t) - e_2(t-1)][e_3(t) - e_3(t-1)]|;$$

and $$M(t) = |m(t-1) + m(t) + m(t+1)|$$

where M(t) is the scalar signal, t is time, and the number 1 is used to indicate the ECG sample taken at the previous or subsequent sampling period. For example, using a sampling frequency of 250 Hz, each sample is taken at 4 millisecond (msec) intervals and, thus, the term (t−1) indicates the sample taken 4 msec prior to the sample taken at time (t). Scalar signal M(t) advantageously can also be obtained using the formula:

$$M(t) = |[e_1(t+1) - e_1(t-2)][e_2(t+1) - e_2(t-2)][e_3(t+1) - e_3(t-2)]|.$$

In signal processing terms, M(t) is the absolute value of the product of three filtered ECG signals, where the filter consists of a conventional 3 point, e.g., 12 msec, boxcar filter. Other filters, for example a conventional matched filter, advantageously can be used to enhance a QRS complex within the digital signals and to suppress noise, as discussed in detail below.

During step S302, scaler signal M(t) is examined to identify possible QRS complexes by locating points where M(t) crosses from below a predetermined threshold FIRST_THRESH (typically 64 in units of the least significant digital bit). When M(t) crosses the predetermined threshold, a maximum value of M(t) is found within a window MAX_FWD_SEARCH (typically 264 msec) starting at the time of threshold crossing. It will be appreciated that checks for the location of maximum M(t) can also be made using a sliding window to verify that the maximum value is accurately identified. The maximum value for M(t) is identified as a possible QRS complex and the time of occurrence, $T_{qrs}$, is stored for use in processes described below. The program then executes step S40 of FIG. 3.

At step S40, the program checks to determine whether a possible QRS complex was located in step S30. If the check is false, the program returns to step S20, while if the check is true the program executes step S50.

Figure 4B:
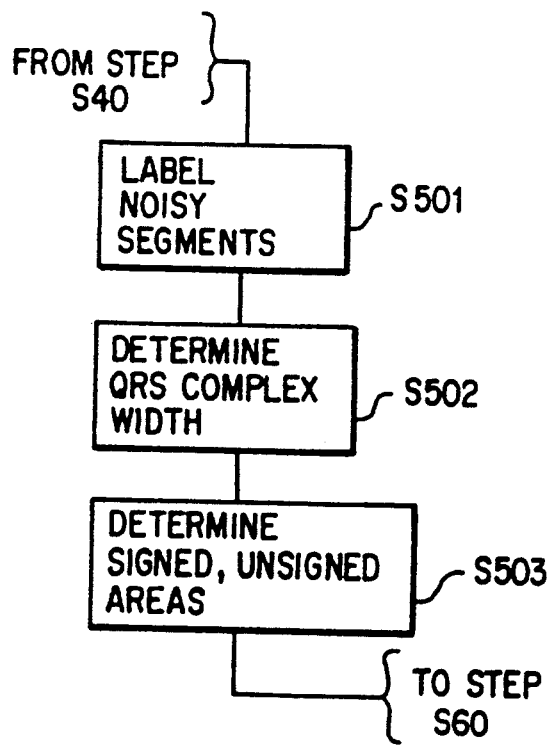

During step S50, the features of the scalar signal produced in step S301 are extracted. Referring to FIG. 4B, at step S501, the scalar signal around each possible QRS complex is analyzed to determine whether the QRS complex should be denoted as noisy or not. For the $i^{th}$ QRS complex, a segment of M(t) is taken over the interval $T_{qrs}(i) - W_{noise} \leq t \leq T_{qrs}(i) + W_{noise}$, where $W_{noise}$ is the half-width of the window used in noise analysis. Thus, a segment, denoted $N_i(t)$, of M(t) centered about $T_{qrs}(i)$ is analyzed for noise. During the analysis, the number of times $N_i(t)$ crosses a possible noise threshold in either direction is counted. The possible noise threshold may be varied as hereinafter described. If the number of crossings is less than a predetermined value MAX_SIGN_CHANGES (typically 24), the QRS complex is deemed to be not noisy and the possible noise threshold becomes the determined noise threshold. If the number of crossings is greater than or equal to MAX_SIGN_CHANGES the noise threshold is adaptively increased by a predetermined value IJ_INCREASE (typically 2 in units of the least significant digital bit) and the noise analysis is repeated. If after a predetermined number of increases in the noise threshold, the noise threshold equals a predetermined maximum noise threshold before the number of crossings becomes less than MAX_SIGN_CHANGES, the segment $N_i(t)$ is deemed noisy and the analysis ends.

The possible noise threshold is varied from a low value to a maximum cutoff value $\bar{\Theta}_{noise}$. The low value is set to a predetermined fraction of the value of the scalar signal M(t) evaluated at a time of occurrence $T_{qrs}$, all averaged with a running average of the previous noise threshold $\Theta_{noise}$ found for the previous beats. The maximum cutoff value is the value of the scalar signal M(t) evaluated at $T_{qrs}$ divided by a PEAK_FACTOR, typically about 6. It will be appreciated that other noise threshold variation processes will be apparent from these teachings to those skilled in the art, and which may be used as a means to search for the threshold at which the above described threshold crossing criteria is met.

During step S502, QRS width, one feature of the scalar signal, is extracted starting with a times series for each QRS complex k using the formula:

$$e_{width}(i) = F^5 \left( \sum_{j=1}^{3} |F(e_j(i + 1 + T_{qrs}[k] - w_{qrs\_width}] - e_j(i + T_{qrs}[k] - w_{qrs\_width}]| \right)$$

for i+1, 2, . . . , $2W_{qrs\_width}$ where $W_{qrs\_width}$ is the half-width of the window used for analyzing the width of the QRS complex and where F() is a conventional box-car filter which spans about 12 msec. $F^5()$ denotes that the box-car filter is applied five times in succession. If the QRS complex was deemed to be noisy in step S501, described above, QRS width is determined using the formula:

$$e_{width}(i) = F^5 \left( \sum_{j=1}^{3} |F(e_j(i + 1 + T_{qrs}[k] - w_{qrs\_width}] - \right.$$

-continued $$e_j[i + T_{qrs}[k] - w_{qrs\_width}]\Big)|*$$

$$\sum_{j=1}^{3} |e_j[i + 1 + T_{qrs}[k] - w_{qrs\_width}]|.$$

A width threshold $\Theta_{qrs\_width}$ is then set to the smallest value which provides less than eight crossings of the width threshold. The width of the $k^{th}$ QRS complex is determined using the formula:

$$\text{width}[k] = T_{offset}[k] - T_{onset}[k]$$

where $T_{offset}[k]$ and $T_{onset}[k]$ are determined from the $e_{width}[i]$ time series and $\Theta_{qrs\_width}$ threshold.

If the width[k] is less than MIN_WIDTH, a predetermined constant, or if $\Theta_{qrs\_width}$ is greater than the product of the peak value of $e_{width}(i)$ and PEAK_PORTION_FRACTION/PEAK_PORTION (typically 6/8ths), then the beat is declared bad and it is removed from further processing.

Each lead signal is filtered again through a F() boxcar filter, and a second derivative of the filter's output signal is taken. The threshold crossing criteria for noisy beat is applied to each lead and the sum of all leads to redetermine if the possible beat should be labeled as noisy and to determine whether or not the possible beat should be removed from further processing for being a bad beat.

At step S503, a plurality of areas are determined for each QRS complex. Each area is defined as the integral of the difference between the QRS complex and the baseline of the QRS complex, where the baseline is given by the formula:

$$B_i[k] = (e_i[T_{onset}[k]] + e_i[T_{offset}[k]])/2$$

where i denotes the channel number of the ECG signal and k denotes the QRS complex. A signed pre-area of a digital signal channel is produced by integrating the difference between the baseline and the QRS complex over a range starting at the onset of the QRS complex and ending at the center of the QRS complex. The center of the QRS complex is the time, between onset and offset, for which the total unsigned pre-area found by integrating the difference between the baseline and the QRS complex starting at the onset and ending at the center is approximately equal t half of a total unsigned area found by integrating starting at the onset and ending at the offset. The total unsigned area and total unsigned pre-area are determined by summing the respective unsigned areas and unsigned pre-areas over all digital signal channels. The center advantageously can be found by carrying out a systematic search of possible values of the center. An unsigned pre-area is determined by integrating the absolute value of the difference between the baseline and the QRS complex. Both signed and unsigned post-areas are obtained in a similar manner.

Under certain circumstances, the beat will be declared bad and removed from further processing. The beat is declared bad if the difference between the value of the raw ECG signal at onset is different from the value of the raw ECG signal at offset by an amount whose magnitude is greater than or equal to the sum of the absolute values of the pre- and post-heights in each lead. The pre and post heights comprise a plurality of measured values, two measured values for each lead being processed. Typically three leads are processed; therefore, there are typically three pre-heights and three post-heights. The pre-height is the maximum amplitude, either positive or negative, of the pre-area for any given lead. The post-height is the maximum amplitude of the post-area for any given lead. The beat is declared bad if the number of crossings at the final threshold chosen for width determination is zero. The beat is declared bad if the width is less than MIN WIDTH. Parameters which are heretofore undefined are hereinafter defined. The program then goes to step S60.

Referring to FIG. 3, at step S60 the features extracted from the scalar signal are plotted in an N-dimensional feature space, where N is equal to the number of features extracted, so as to form clusters of QRS complexes. In addition, a cluster list is updated during step S60, as hereinafter discussed. It will be appreciated that, since three channels are either received, interpolated or extrapolated from the ECG signals, and since a total of four areas are determined for each channel in addition to the width of the QRS complex, a total of thirteen dimensions are used to form the feature space. The features of any individual QRS complex, however, do not indicate whether or not the QRS complex is normal. In order to determine if a QRS complex is normal, it is compared with other QRS complexes, i.e., the QRS complex is compared with the shape and the timing of the QRS complexes stored in clusters within the features space.

The features extracted for each QRS complex are compared to the features extracted from the previous QRS complexes in the following manner, termed clustering.

A list of existing clusters is stored in RAM 30 which includes information about the position of that cluster in the feature space (e.g., average of features of QRS complexes in the cluster), the typical forward and backward coupling intervals (e.g., average values) of the QRS complexes that have been located in the cluster, the number of QRS complexes that have been located in the cluster, and the labels of the QRS complexes that have been located in the cluster. A forward and backward coupling interval is the time between a QRS complex and the next and previous QRS complex, respectively. In addition, the list contains the $T_{qrs}$ time at which the first and the most recent QRS complex was located in the cluster, togetherness count of the number of times two QRS complexes in succession are added to the cluster, as well as a cluster label declaring the type of the cluster, e.g., Unknown, Normal, PVC or deleted. At the start of the analysis of an ECG record, there are no clusters listed. Clusters are formed in the following manner.

For each possible QRS complex identified, the features of that QRS complex are compared to the features of each cluster in the list of the clusters. If there are no clusters in the list, a new cluster is made which is given the feature position of the QRS complex's features, the backward coupling interval of that QRS complex and the time of the first and most recent QRS complex located in the cluster is set to the time of the possible QRS complex. The number of QRS complexes in the cluster is set to 1, and the label is set to unknown. This new cluster is added to the cluster list.

If there are clusters in the cluster list, then the distance between the QRS complex's features and each cluster's position in the feature space is found. The cluster which is closest to the QRS complex is identified. If the closest cluster is less than MAX_DX, the QRS complex is entered into the closest cluster. This involves incrementing the number of QRS complexes in the cluster, e.g., the population of the cluster, updating the cluster's position in the feature space by taking an average of the cluster's previous position and the QRS complex's features (preferably ⅞ths weight is applied to the cluster's previous average position and ⅛th weight is applied to the new QRS complex's position), similarly updating the forward and backward coupling intervals and incrementing the togetherness count as indicated. If there is no cluster closer to the QRS complex's features then MAX_DX (typically 400), a new cluster is created and added to the cluster list, as hereinbefore described.

As new clusters are created, the cluster list grows. When the length of the list reaches a predetermined length, an old cluster is deleted for each cluster added to the list, so that the length of the list remains constant. Preferably, the maximum number of clusters listed is a predetermine value of about sixteen so as to enhance resolution without degrading analysis efficiency. Preferably, the cluster chosen for deletion is that which least recently had a QRS complex entered into it and which has a population less than the populations of two thirds of the clusters on the list. The program then executes step S70, which increments COUNT by one.

During step S80, a check is made to determine if flag FF is equal to zero. If true, the program goes to step S90, described in detail below. If false, the program executes S110 to determine if enough putative QRS complexes, the predetermined number WARM_UP_COUNT of QRS complexes after system start, have been collected and plotted within the feature space. Preferably, the QRS complexes are initially clustered in the feature space without attempting to label either the clusters or individual QRS complexes. If the value for COUNT is less than WARM_UP_COUNT, the program executes step S20 and additional QRS complexes are obtained as described above. After the total number of QRS complexes located exceeds WARM_UP_COUNT, e.g., when executes the step S120 to analyze each of the clusters so as to identify those clusters corresponding to a normal QRS.

At step S120, a first check is made for merger to identify the cluster having the largest population. Since other nearby clusters can have similar features, the distance between the largest cluster and all other clusters is determined. If the distance between the largest cluster and another cluster is less than a predetermined distance MAX_DX, the two clusters are merged by averaging the averages, taking the maximum of the maximums, the minimums of the minimums, the most recent addition of QRS is set to the more recent of the two clusters, etc.

When the population of the largest cluster is very large in comparison to that of the other clusters, e.g., when the population is greater than a predetermined value MIN_INI_NSR_POP (typically WARM_UP_COUNT/2), the cluster is labeled normal and a normal beat rhythm state is set to TRUE. If the population in the largest cluster is less than MIN_INI_NSR_POP, bigeminy may be occurring. Bigeminy is located by identifying the largest and second largest clusters and determining an average backwards coupling interval for each cluster, where the backwards coupling interval is the time between the present QRS complex and the previous QRS complex. When the shorter backwards coupling interval is less than about 0.75 times the longer backwards coupling interval, the shorter coupling interval is less than ⅞ times the average backwards coupling interval, i.e., the average of the short and long backwards coupling intervals, the populations of both clusters are less than a predetermined value MAX_INI_BGM_TOG (typically WARM_UP_COUNT/8), and the sum of the populations of both clusters is less than a predetermined value MIN_INI_BGM_TOG, bigeminy is occurring. In this case, the cluster having the longest backwards coupling interval is labeled normal, while the other cluster is labeled PVC, the bigeminy state is set to TRUE and the normal beat rhythm is set to FALSE. If the conditions for labeling clusters described above are not satisfied, the largest cluster will be labeled normal if (i) POP_SUM, the total population of all the clusters is less than WARM_UP_COUNT, (ii) the population of the largest cluster is greater than twice the population of the second largest cluster and (iii) the population of the largest cluster is greater than half of the POP_SUM. In this case, the bigeminy state is FALSE and the normal beat rhythm state is TRUE.

In the event that one of the clusters cannot be given a normal label, as tested in step S130, the program steps to step S20 via step S150 after setting WARM_UP_COUNT to WARM-UP-COUNT plus LEARNCOUNT, thereby collecting another WARM_UP_COUNT number of QRS complexes. If step S130 is true, flag FF is set equal to zero and the population of all other clusters is set equal to one at step S140 and step S20 is executed.

As flag FF is set equal to zero in step S140, cluster learning is concluded and several additional one time initialization steps occur. Except when bigeminy exists, the populations of all clusters, except the cluster labeled normal, are set equal to one. When bigeminy exists, the populations of all cluster, except the ones labeled normal and PVC, are set equal to one.

Parameters of a normal QRS complex are established. The width, signed area, average NN time interval and average RR time interval are established for an average normal QRS complex. The width of the average normal QRS complex is set equal to the average width assigned to the normal cluster. The signed area of the average normal QRS complex is set equal to the average signed area assigned to the normal cluster. The average NN time interval of the average normal QRS complex is set equal to the average of the average backward coupling interval and the average forward coupling interval of the normal cluster when bigeminy does not exist, and it is set equal to the average of the average backward coupling interval of the longer cluster and the average backward coupling interval of the shorter cluster, when bigeminy exists. The average RR time interval is set equal to the average NN time interval.

As new possible QRS complexes are detected subsequent to cluster learning, they are clustered and labeled. There may come a point when there are a sufficient number of new QRS complexes in an unlabeled cluster to confidently give the cluster a label. There are several cluster label possibilities, for example: a cluster may be labeled as normal, as PVC, or as deleted.

When a QRS complex that belongs to an unlabeled cluster is labeled normal, the rules described hereinafter may cause the unlabeled cluster to be labeled normal, but this occurs only if the cluster's total population is greater than MIN_NEW_NORMAL_POP (typically 10) and either the number of normal QRS complexes in the cluster is greater than half of the cluster's total population, or the number of normal QRS complexes in the cluster is greater than four times the number of abnormal QRS complexes in the cluster.

When a QRS complex that belongs to an unlabeled cluster is labeled PVC, the rules described hereinafter may cause the unlabeled cluster to be labeled the same as the QRS complex, but this occurs only if the cluster's total population is greater than MIN_NEW_ABNORMAL_POP (typically 6) and either the number of abnormal QRS complexes in the cluster is greater than half of the cluster's total population, or the number of abnormal QRS complexes in the cluster is greater than twice the number of normal QRS complexes in the cluster.

When a QRS complex that belongs to a unlabeled cluster is labeled deleted, the rules described hereinafter may cause the unlabeled cluster to be labeled deleted, but this occurs only if the total number of QRS complexes in the cluster is greater than MIN_NEW_DELETE_POP (typically 6) and the number of deleted QRS complexes in the cluster is greater than half of the total number of QRS complexes in the cluster.

Extraneous circumstances, such as patient movement, cause new QRS complexes to be detected subsequent to cluster learning. Existing clusters become replaced by many new clusters created because of a noisy segment in the data when the patient has a very bizarre rhythm. When this condition occurs, the populations of the clusters are reset to 1 and the cluster labels are deleted. Thereafter, as new possible QRS complexes are identified, relabeling of clusters will occur.

As new possible QRS complexes are detected and labeled subsequent to cluster learning, global rhythm and morphology information is updated including: avgNN, avgNW, avgNSS and avgRR. Whenever a beat is labeled normal, avgNN is updated. The value of avgNN is updated to be (7*avgNN+RR)/8 where avgNN is the present value of avgNN and RR is the time between the normal beats. When a beat is labeled normal, avgNW and avgNSS are updated. The value of avgNW is updated to be (7*avgNW+width)/8 where width is the measured width of the present normal beat. The value of avgNSS is updated to be (7*avgNSS+SAS)/8 where SAS is the signed area sum of the present normal beat, being the sum of the pre-areas and post-areas for all leads. Whenever a beat is detected, whether it is labeled normal or PVC, avgRR is updated to be (7*avgRR+rr)/8 where rr is the time between the current beat and the previous beat.

The patient's rhythm state is evaluated to be either (1) normal with reasonably regular coupling intervals, (2) irregular with variable coupling intervals, (3) unusual with variable coupling intervals and a fair number of new clusters being formed or (4) bizarre with highly variable coupling intervals and a lot of new clusters being formed. The variability of the coupling intervals is determined based on the RR interval and not the NN interval. If the criteria for the individual patient state is determined, then the state is TRUE; otherwise, the state is FALSE. The states are prioritized from normal to bizarre, with bizarre having the highest priority. Thus, a bizarre state will be declared rather than an unusual state if the criteria are met for bizarre. Each time a state is declared, this declaration is indicated to an output and a time constant called RHYTHM_COUNT is set. Each state is set to this value when the state is first detected. As each new beat is processed, the state count is decremented. A new output indication will not be generated until first the respective state count has been decremented to zero and second the criteria for the respective state are met. Only beats which are labeled, not deferred labelling, are processed to determine patient rhythm state.

For processing a beat, the cluster list is scanned to assess the rate at which clusters are being created. Cluster creation rate is determined by counting the number of clusters in the cluster list that are less than RECENT_SHAPES (typically 32) in age.

If the patient is already in a strange rhythm state (bizarre or unusual) and the criteria for strange rhythms (i.e., many new clusters generated and irregular intervals) are no longer met, the rhythm state resets to normal rhythm state and begins relearning. If either bizarre state or unusual state is not FALSE and the recent shape count is less than a shape_count_LO_THRESHOLD (typically 5) and an RR difference count is less than an RRdif_LO_THRESHOLD (typically 5), then relearning may be appropriate. If relearning may be appropriate and bizarre state is true, then relearning is initiated by setting the cluster populations to one and setting the normal, abnormal and delete counts to zero. Then the normal state is set to RHYTHM_COUNT (typically 100), irregular state is set to FALSE, unusual state is set to FALSE and bizarre state is set to FALSE.

The next highest priority is a test for the bizarre state. If the bizarre state is FALSE and the recent shape count is greater than or equal to the shape_count_HI_THRESHOLD (typically 10) and the RR difference count is greater than or equal to the RRdif_count_HI_THRESHOLD (typically 9) then the bizarre shape is set to RHYTHM COUNT, normal state is set to FALSE, irregular state is set to FALSE and unusual state is set to FALSE.

Otherwise, if the unusual state or the bizarre state is FALSE and the recent shape count is greater than the shape count low threshold and the RR difference count is greater than or equal to the RRdif_count_LO_THRESHOLD, then the unusual state is set to RHYTHM_COUNT, normal state is set to FALSE, irregular state is set to FALSE, and bizarre state is set to FALSE.

Otherwise, if the irregular state is FALSE and the RR difference count is greater than or equal to the RRdif_count_LO_THRESHOLD and the recent shape count is less than the shape_count_LO_THRESHOLD, then the irregular state and relearning may be set. If the irregular state and relearning may be set and the bizarre state is set, then relearn is initiated by setting cluster populations to one and setting normal, abnormal and delete counts to zero. Then the irregular state is set to RHYTHM_COUNT, normal state is set to FALSE, unusual state is set to FALSE and bizarre state is set to FALSE.

The above criteria tests are performed on each valid labeled beat. After the above tests have been performed, the irregular state count is decremented if greater than zero, the unusual state count is decremented if greater than zero, and the bizarre state count is decremented if greater than zero. Finally, the unnormal state is set to be TRUE if either the bizarre state is TRUE or the unusual state is TRUE.

As new possible QRS complexes (beats) are detected subsequent to cluster learning, rhythm and morphology boundaries are established prior to analysis of each beat. The parameter early and late are defined to be 7*avgNN/8 and 3*avgNN/2, respectively. The parameters early_fusion and late_fusion are defined to be 7*avgNN/8 and 9*avgNN/8, respectively. The parameters low_c_pause and hi_c_pause are defined to be 29*avgNN/16 and avgNN+late, respectively. The parameters wide and narrow are defined to be 5*avgNW/4 and 5*avgNW/8, respectively. The parameter Twv_RR is the latest a T-wave can occur and typically set to 350 msec. The parameter PZ_DUR is the length of time between beats required to declare a pause and is typically set to 2.5 sec. The parameters NN TOL and NNZ_TOL are the tolerance for comparing RR interval to the avgNN for non-noisy beats and noisy beats, respectifully, and are typically set to 48 msec. and 96 msec, respectfully.

As new possible QRS complexes are detected, some of these detections may be identified as a bad beat and removed from further processing. The beat is declared bad if the RR-interval for this beat is less than earlyT, and LowHeight() is true, and the number of sign changes determined during noise detection is greater than SIGNCH_NOBEAT (typically 5), and the number of sign changes in the second derivative of the signal in the window used for width determination is greater than SUM123_NOBEAT (typically 13), and the total unsigned area in all leads is greater than SUMU_NOBEAT (typically 12500). It will be appreciated that an area is the sum of the samples over a time interval, where the sample rate is 250 Hz typically. It will also be appreciated that an analog signal from a lead is amplified before being converted to a digital signal, and that the amplification gain is adjusted according to an automatic gain control. The beat is declared bad if LowHeight() is true and width is greater than WIDTH2_NOBEAT (typically 160 msec). The beat is declared bad if the RR-interval is less than 200 msecs and the previous beat was normal. The beat is declared bad if the previous beat was normal, and the RR-interval is less than earlyT, and width is less than narrow+NW_TOL (typically 16 msec.), and LowHeight() is true, and the number of sign changes determined during noise detection is greater than SIGNCH_NOBEAT (typically 5) NWZ_TOL is typically twice NW_TOL.

At step S90, a plurality of rules, for example the rules shown in Table 1, are applied to possible QRS complexes within the digital signal so as to label each QRS complex, e.g., as a normal QRS complex, an abnormal QRS complex (i.e., one not labeled normal or deleted) or a deleted QRS complex. The rules are weighted so that a QRS complex located within a labeled cluster is preferentially assigned the cluster's label. Preferably, each QRS complex is labeled as it is received. However, in certain cases it is not possible to assign a label immediately and the labeling of QRS complexes is deferred until additional QRS complexes are received. The maximum number of QRS complexes which can be deferred is a predetermined number, e.g., five, giving a total of six unlabeled QRS complexes. When a total of six unlabeled QRS complexes exist, all six are forced to be labeled as hereinafter described. The labeling rules shown in Table 1 are applied in the listed order depending on the number of deferred QRS complexes. For instance, the one beat case has no deferred beats, and the two beat case has the present beat plus one deferred beat. Each of the terms of the left hand column of Table 1 is an assertion, with the number(s) in () indicating the QRS complex(es) to which the assertion applies. The lowest numbered QRS complex is the earliest QRS complex within a group. For example, NormL(1) asks if the earliest QRS complex is a member of a normal cluster while NormL(5) asks if the fifth QRS complex is a member of a normal cluster. NormT(3-2) asks if the difference in time of occurrence between the 3rd and 2nd QRS complex in the group is in the normal range, and notation like NormT(2) is shorthand for NormT(2-0) where the zeroth QRS complex is the QRS complex that occurred just before the sequence of beats under consideration. In Table 1, "&&[ represents the logical AND while " || " represents the logical OR. The assertions deal with the cluster in which the QRS complex is located, the noise content of the QRS complex, the morphology of the QRS complex, the timing of the QRS complex and the general rhythm of the digital signals.

A beat labeled according to the plurality of rules contained in Table 1 will be categorized into one of normal, T-wave, deleted, abnormal and unlabeled. It will be appreciated that although the labeling orders on the right hand side of Table 1 label according to a variety of labels, all labeling orders that are not either deferred, normal, T-wave or unlabeled, are categorized as abnormal. For example, SVPCWP (for super ventricular premature contraction with pause) is categorized as abnormal. SVPC (for super ventricular premature contraction), VentESC (for ventricular escape beat), PVC (for premature ventricular contraction), SupV (for super ventricular), fusion, and funny are all categorized as abnormal beats. It will be appreciated that SetQ() is not a labeling order and is a function as herein described.

Assertions related to cluster location include assertions in the form NormL(), NoL(), PVCL() and DelL(), which ask if the QRS complex is located within a cluster labeled normal, not labeled, PVC and deleted, respectively. SameCluster(a,b) asks if QRS complexes a and b belong to the same cluster. SmallPop() asks if the population of the cluster in which the QRS complex is located is less than a predetermined value MIN_NEW_NORMAL_POP.

Assertions related to the noise content include Noisy() and NotNoisy(), which ask if the segment in which the QRS complex was located has been deemed to be noisy, as discussed in greater detail above.

Assertions dealing with the morphology of the QRS complex include WideW(), NormW(), N2W() and NNoiseW(). WideW() is true if the width of the QRS complex is greater than wide, where wide is defined to be [5×avgNW]/4. NormW() is true if the QRS complex width is between wide and narrow, where narrow is initially set to be [5×avgNW]/8, with avgNW being updated to [7×avgNW+width]/8 after two consecutive normal beats are received. N2W() and NNoiseW() are true when the width of the QRS complex is within the range avgNW±NW_TOL and avgNW±NWZ_TOL, respectively, where NW_TOL and NWZ_TOL are predetermined tolerance values (typically 16 and 32 msec., respectively).

LowHeight() is true if the height of the QRS complex is less than a predetermined value MIN_HEIGHT (typically 300 times the minimum A to D step height). DiffAreaSign(a,b) is true when the signs of the signed pre-areas are different for a and b or the signed post-areas are different for a and b, in any lead.

AbnormalRhythm is an infrequently asked assertion that is true when the patient has an unnormal rhythm state (when many small clusters were recently created). It is true when the patient rhythm state is either bizarre or unusual.

Figure 5:
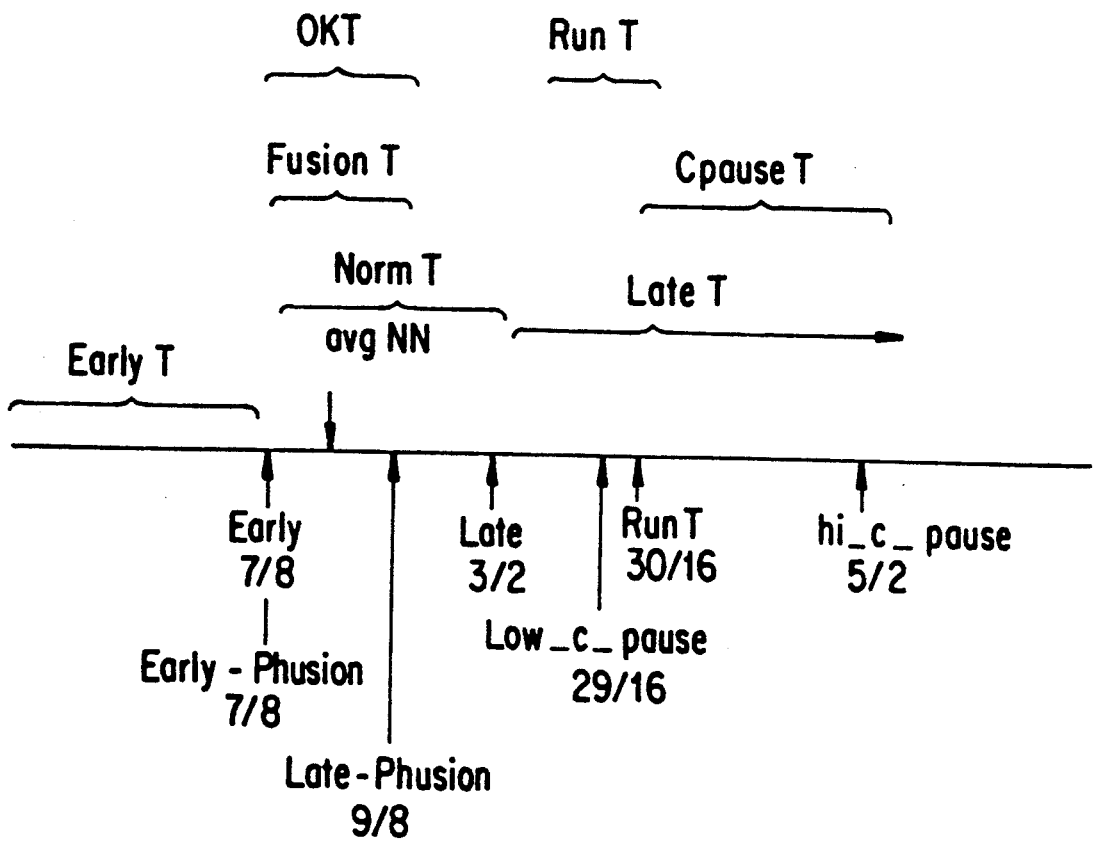
FIG. 5 shows a timing pattern for QRS complex evaluation according to step S90 of FIG. 3.
Figure 5B:
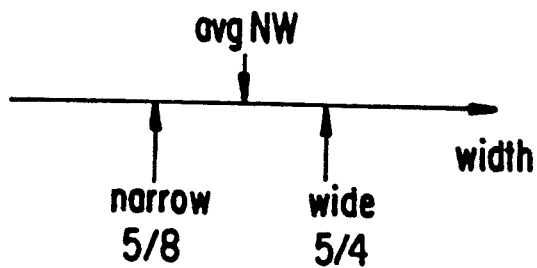
FIG. 5B shows average QRS width and normal boundaries.

Assertions related to timing deal with the RR intervals between QRS complexes. Referring to FIG. 5, a plurality of ranges centered about avgNN which are used in evaluating assertions dealing with time are shown. In FIG. 5, terms below the line indicate end point values based on avgNN. Ranges shown above the line are formed from the values below the line. For example, NormT() is true if the RR-interval falls between early, $\frac{1}{2} \times$ avgNN, and late, $3/2 \times$ avgNN. EarlyT() and LateT() are true if the RR-interval is less than early or greater than late, respectively. GoodT() is true (for good timing) if the RR-interval is between early and late. FusionT() is true if the RR-interval is between Early_fusion and late_fusion, OKT() is true if the RR-interval is between early and late_fusion and CPauseT() is true if the RR-interval is between low_c_pause and hi_c_pause. LT_c_PauseT() is true if the RR-interval is less than low_c_pause. RunT() is true if the RR-interval is less than avgNN plus early. Certain timing assertions deal with whether or not the RR-interval is within a predetermined tolerance of avgNN. For example, NNT() and ZNNT() are true if the RR-interval is within the range of avgNN±NNTOL, where NNTOL is about 48 msec., and avgNN±NNZTOL, where NNZTOL is about 96 msec. SlateT() and SearlyT() are true if the RR-interval is within the range of avgNN±[NNTOL/4]. Finally, LongPauseT() is true if the RR-interval is greater than a predetermined value PZ_DUR, e.g., about 2.5 sec., while TwaveT() is true if the RR-interval is less than a predetermined value Twv_RR, e.g., about 350 msec.

Referring to FIG. 3, the number of deferred QRS complexes is determined and the rules for the appropriate case are applied to the QRS complex requiring labeling, with the exception of the six beat case, which is hereinafter discussed. If the evaluation of all of the assertions in a line in the left hand column are true, the QRS complexes are labeled as shown in the right hand column on the same line. For example, if OKT(3) in the three beat case is true, the latest QRS complex is labeled a normal QRS complex while the two previous QRS complexes are labeled deleted. In the three beat case, the latest QRS complex is beat 3. The labeling orders in the right hand column D(), N(), PVC, and F(), for example, indicate that the 0$^{th}$ QRS complex should be labeled deleted, normal, PVC and fusion, respectively. Labeling orders such as D() indicate that the cluster in which the QRS complex is located should be labeled according to the ClusterUpdate rules hereinafter discussed.

SetQ() indicates a set of additional rules to direct labeling when a beat has not been classified and the beat before and the beat after may not have been classified. These rules applied to SetQ(p) are understood within the context of the following definitions. RR is the time interval between beat p and beat p−1. CRR is the RR time corrected for the beat centers as hereinbefore described. RR2 is the time interval between beat p−1 and beat p+1. Beat p acquires the label of the cluster within which it is located if: NotNoisy(p) && NotNoL(p) is true. Otherwise, beat p is labeled normal if:

$$(5 \cdot avgNN/8 < RR < 58 avgNN/4)(NNoiseW(p))$$
$$(avgNN - NNZ\_TOL < CRR < avgNN + NNZ\_TOL)$$
$$(avgNW - NNZ\_TOL < \text{beat } p \text{ width} < avgNW + NNZ\_TOL)$$

is true.
Otherwise, beat p is labeled PVC if:

$$(7 \cdot avgNN/4 < RR2 < 5 \cdot avgNN/2)(RR < 7 \cdot avgNN/8)$$
$$\text{Not } (vgNW - TOL < \text{beat } p \text{ width} < avgNW + TOL)$$

is true, where TOL is 5 at the described sampling rate. Otherwise, if unnormal_state is false, determine whether the timing is so early that it can be called a T-wave. The putative beat is a T-wave if the RR interval between the current putative beat and the prior beat is less than 350 msec. If it is a T-wave, it is labeled deleted. Otherwise, label beat p as suspicious if:

NotAbnormalRhythm is true.

Otherwise, update the beat's cluster as if the beat were a PVC beat if:

RR<7*avgNN/8 is true.

Otherwise, update the beat's cluster as if the beat were a normal beat if:

RR<3*avgNN/2 is true.

Otherwise, relabel the beat as a PVC beat and update the beat's cluster accordingly.

It will be appreciated that the labeled clusters can contain QRS complexes having labels different than the cluster label.

In the case where six QRS complexes require labeling, additional rules advantageously are applied to iteratively attempt to label the complexes. First, a check, NormL(6) && NormL(5) && GoodT(6-5) is applied, which, if true, orders SetQ(1), SetQ(2), SetQ(3), SetQ(4), N(5) and N(6) labels to be assigned to the six beats. If the check is not true, the program looks to see if the beats, starting with the most recent QRS complex, are located within labeled clusters. This process is repeated iteratively. The beat under consideration is beat n.

The program checks each QRS complex (beat n) to see if NormL(n) is TRUE, and if so, the beat is labeled N(n) and the next beat is processed. If NormL(n) is FALSE, the program checks the beat to see if it is actually a T-wave of the ECG signal. If both NotGood(n-(n-1)), where n is the QRS complex of interest and n-1 is the previous QRS complex, and LowHeight(n) are true, the n$^{th}$ QRS complex is a T-wave and labeled deleted.

Finally, the program checks to see if the QRS complex is approximately normal. The QRS complex is approximately normal if (i) either Noisy(n) is true and PVCL(n) is false or the width of the n$^{th}$ QRS complex is between narrow and wide+NW_TOL, where NW_TOL is a predetermined tolerance value, and (ii) the sum of the signed areas for all leads is between [3×avgNSS]/4 and [5×avgNSS]/4, where avgNSS is the average of the sum of the signed pre-areas and the signed post-areas of the QRS complexes located in the normal cluster.

If the beat is approximately normal, the program determines if it can be labeled normal. The program looks for the $m^{th}$ QRS complex such that the difference between the RR-intervals of QRS complex n and QRS complex m is greater than early—NN_TOL, where NN_TOL is a predetermined value. If m and n are adjacent QRS complexes, i.e., m=n−1, then the label N(n) is assigned. However, if there are putative QRS complexes between the beats m and n, the following rules are applied to the intermediate QRS complexes. If Noisy() or LowHeight() is true, then the QRS complex label D() is assigned. And if not, then if AbnormalRhythm is true, then the label PVC() is assigned, and if not, then if the beat's cluster has a label, the beat is labeled according to the label of its cluster, and if not, then the QRS complex is labeled suspicious.

After all six beats have been considered iteratively, starting from the most recent beat and ending with the earliest beat, a second stage labeling process is entered to again consider all six beat iteratively, this time processing beats starting from the earliest beat to the most recent beat. The beat under consideration is number p.

If the beat has been labeled earlier, bypass the beat and takeup the next successive beat. If p<6, and NotNormW(p) is true, and EarlyT(p) is true, and NotNoisy(p) is true, and the interval between p and p+1 is greater than early fusion then make the label PVC(p). If p<6 and NoL(p+1) is true then make the label N(p). Otherwise, if NoL(p+1) is true, and NotNormW(p) is true, and NotNormW(p+1) is true, and TwaveT((p+1),p) is true, and DiffAreaSign (p,(p+1)) is true, then make labels PVC(p) and D(p+1). Otherwise, if Noisy(p) is true or LowHeight(p) is true, then make the label D(p). Otherwise, if AbnormalRhythm is true, then make the label PVC(p). Otherwise if NoL(p) is false, then label the beat with the label of the cluster in which the beat is located. Otherwise, if either the normal population or the abnormal population of the cluster in which the beat is located is greater than MIN_NEW_NORMAL POP/2, then label the beat abnormal if the abnormal population is greater than the normal population and label the beat as normal if the abnormal population is not greater than the normal population. Otherwise, label the beat as suspicious. The program then executes step S100.

When a beat labeling order is underscored, then the cluster to which the beat belongs may be updated according to a category of the label of the beat, the categories being: Normal if the beat is labeled normal, Abnormal referring to any genuine QRS complex label including PVC, and Delete referring to non-genuine QRS complexes such as T waves or noise. When updating a cluster according to a Normal beat, the normal population of the cluster is incremented, and a test is applied to see if the cluster can be labeled normal, which test is the same test as is applied as if the cluster were unlabelled as hereinafter described. When updating a cluster according to an Abnormal beat, the abnormal population of the cluster is incremented, and a test is applied to see if the cluster can be labeled abnormal, which test is the same test as is applied as if the cluster were unlabeled as hereinafter described. When updating a cluster according to a Delete beat, the delete population of the cluster is incremented, and a test is applied to see if the cluster can be labeled delete, which test is the same test as is applied as if the cluster were unlabeled as hereinafter described.

At step S100, cluster labeling is performed after one or more QRS complexes are labeled according to the ClusterUpdate rules hereinbefore discussed. When a QRS complex is labeled normal, the associated cluster is labeled normal if the total population of the cluster is greater than a predetermined value MIN_NEW_NORMAL_POP and normal population, e.g., the number of normal labeled QRS complexes in the cluster, of the cluster is greater than half the total population of the cluster. The cluster is also labeled normal if the total population of the cluster is greater than MIN_NEW_NORMAL_POP and the normal population is greater than four times the abnormal population of the cluster. When a QRS complex is labeled PVC, the associated cluster is labeled PVC if the total population of the cluster is greater than a predetermined value MIN_NEW_ABNORMAL_POP and PVC population count of the cluster is greater than half the total population of the cluster. The cluster is also labeled PVC if the total population of the cluster is greater than MIN_NEW_ABNORMAL_POP and the PVC population is greater than twice the normal population of the cluster. Finally, when a QRS complex is labeled deleted, the associated cluster is labeled deleted if both the total population of the cluster is greater than a predetermined value MIN_NEW_DELETE_POP and the deleted population count of the cluster is greater than half the total population of the cluster. The program then goes to step S20 to collect additional ECG signals.

According to a second preferred embodiment of the method of the present invention, the system 1 is configured as shown in FIG. 2. The operation of the system is shown in the flow chart of FIG. 3. In the second preferred embodiment, system 1 operation, shown generally by step S30 of FIG. 3, is implemented as shown in FIG. 6.

Figure 6:
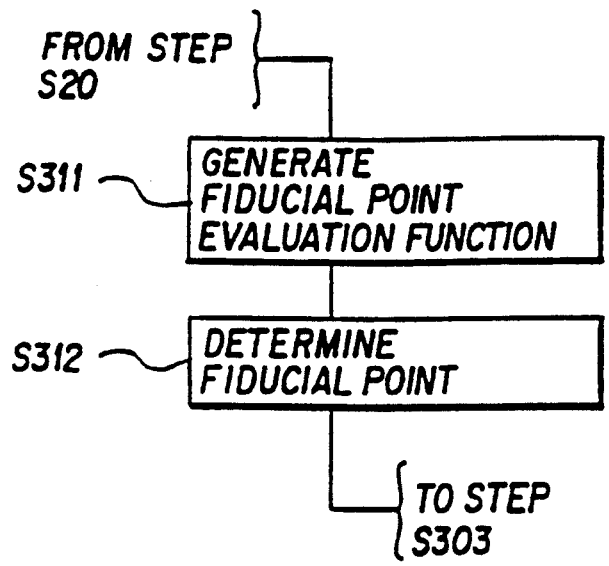
FIG. 6 shows a low level flow chart according to the second preferred embodiment of the present invention implemented by step S30 of FIG. 3.

Referring to FIG. 6, at step S311, a fiducial point evaluation function Q(i) is produced using the formula $Q(i) = Q(f_a(i), f_b(i), f_c(i), f_d(i))$, where $f_a(i)$, $f_b(i)$, $f_c(i)$ and $f_d(i)$ are outputs of the ECG signal applied to filters implementing basis vectors as hereinafter discussed in detail. According to the second preferred embodiment, the fiducial point evaluation function is given by the formula:

$$Q(i) = A|f_a(i)| + B|f_b(i)| + C|f_c(i)| + D|f_d(i)|$$

where A, B, C and D are predetermined constants.

Figure 7:
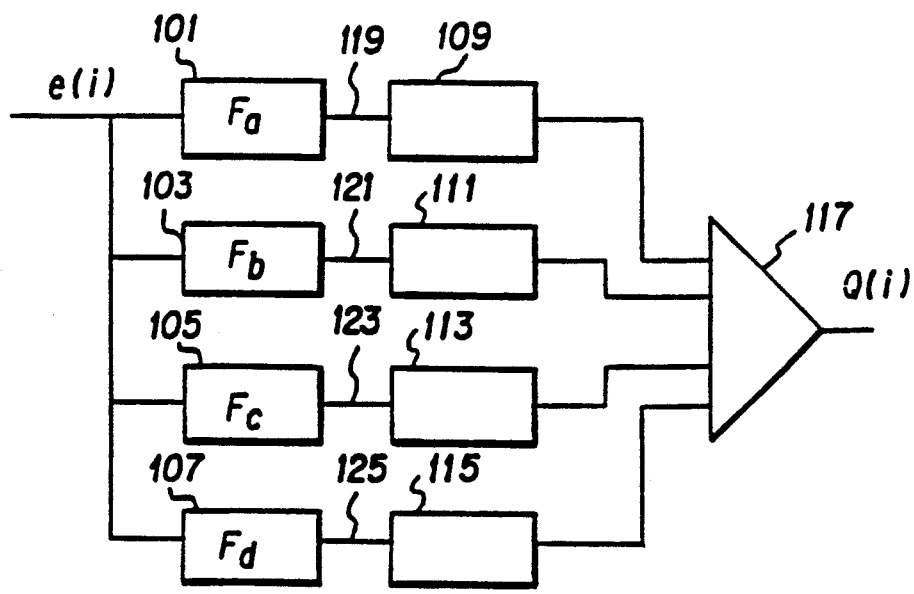
FIG. 7 shows an information flow diagram according to a second preferred embodiment of the present invention implemented in operational step S30 of FIG. 3.
Figure 8A:
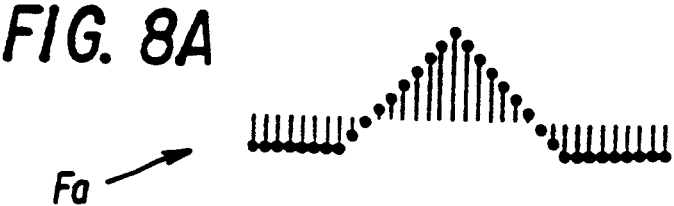
FIG. 8 shows schematic representations of the outputs of the basis filters of FIG. 7 according to the second preferred embodiment of the present invention.
Figure 8B:
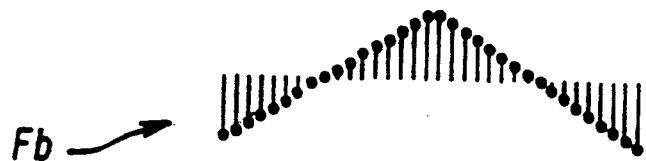
Figure 8C:
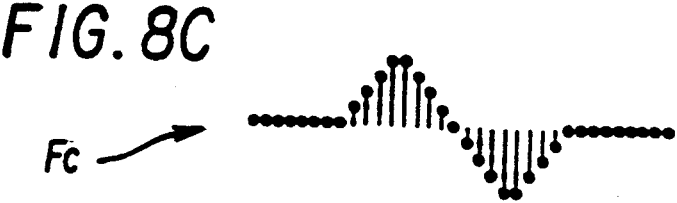
Figure 8D:

Referring to FIG. 7, an information flow diagram is shown illustrating the operation of step S311. A QRS detection and feature extraction system 2, which advantageously can be provided by software stored in ROM 28 of microprocessor 22, comprises a first, second, third and fourth filters 101, 103, 105 and 107, respectively, for generating a feature based on a received digital signal, first, second, third and fourth full wave rectifiers 109, 111, 113 and 115, respectively, each rectifier receiving the output of a corresponding filter, for rectifying the feature, and a summer 117 for combining the rectified features into a single output, i.e., a combined feature or Q(i). Preferably, system 2 includes output terminals 119, 121, 123 and 125, corresponding to filters 101, 103, 105 and 107, respectively, so as to provide feature output for processing similar to that discussed for step S60 above. Preferably, each filter 101, 103, 105 and 107 implements a different basis vector, for example, the basis vectors shown in FIG. 8. Other basis vectors advantageously can be implemented by filters 101, 103, 105 and 107 or a larger number of basis vectors can be implemented by filters 101, 103, 105, 107 and additional filters, not shown. It will be appreciated that, while system 2 is implemented by software in microprocessor 22, system 2 advantageously can be provided using dedicated circuit components.

The basis vectors are selected so as to produce a filter output corresponding to the shape of the QRS complex within the digital signal. As shown in FIG. 7, each of the filters receives the same digital signal but produces a characteristic output different from the outputs of all the other filters. Preferably, basis vectors are piece wise linear and comprise a small number of line segments. The basis vectors advantageously filter out noise, particularly AC line noise and baseline drift. The basis vectors advantageously are implemented at a sampling frequency of 250 Hz with a vector window having a range between about 100 to 200 msec. Thus, filters 101, 103, 105 and 107 produce outputs for every point of the incoming digital signal, which advantageously allows selection of a fiducial point, e.g., $T_{qrs}$, based on the features.

Rectifiers 109, 113 and 115 advantageously produce a rectified feature, i.e., the absolute value of the output of the corresponding filter. Preferably, the outputs of all of the rectifiers are collected at summer 117, which produces the summed output of the features, e.g., Q(i).

During step S312, fiducial points are selected from the fiducial point evaluation function Q(i) by locating local maximums of Q(i). In this embodiment, the time series Q(i) serves the same function served by M(t) in step S302 in order to find the local maximum of Q(i). For each local maximum identified a fiducial point $T_{qrs}$ is identified. Thus, $T_{qrs}$ is obtained when the features produced by the basis vectors are a maximum. The program then executes step S40 of FIG. 3. The operation of system 1 according to the second preferred embodiment is identical throughout the remaining steps shown in FIG. 3, and are not discussed further.

It will be appreciated that system 2 of FIG. 7 can be used with other ECG evaluation systems and arrhythmia detection systems. The output of system 2 advantageously is a plurality of features which can be plotted in an N-dimensional feature space and used for clustering as hereinbefore discussed in detail.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

TABLE 1

| RULES | QRS COMPLEX LABELING |
|---|---|
| ONE BEAT CASE | |
| NormL(1) && Noisy(1) | N(1) |
| NormL(1) && NotNoisy(1) && NotEarlyT(1) NotNormL(1) && NotNoisy(1) && NormT(1) && N2W(1) | N(1) |
| Otherwise | Defer |
| TWO BEAT CASE | |
| EarlyT(2) | Defer |
| OKT(2) && DelL(1) | D(1),N(2) |
| OKT(2) && NoL(1) && NNT(2) && NormW(2) && NotNoisy(2) | D(1),N(2) |
| OKT(2) && NoL(1) && LowHeight(1) | D(1),N(2) |
| NormL(2) && NormL(1) && EarlyT(1) | SVPCWP(1),N(2) |

TABLE 1-continued

| RULES | QRS COMPLEX LABELING |
|---|---|
| && CPauseT(2) | |
| NormL(2) && NormL(1) && EarlyT(1) && LT_C_Pause(2) | SVPC(1),N(2) |
| NormL(2) && NotNormL(1) && NormT(2-1) && NoL(1) && SmallPop(1) && NormW(1) | N(1),N(2) |
| NormL(2) && NotNormL(1) && NormT(2-1) && FusionT(1) && WideW(1) | F(1),N(2) |
| NormL(2) && NotNormL(1) && NormT(2-1) && LateT(1) | VentEsc(1),N(2) |
| NormL(2) && NotNormL(1) && CpauseT(2) && EarlyT(1) | PVC(1),N(2) |
| NormL(2) && NotNormL(1) && LT C PauseT(2) && PVCL(1) | Funny(1),N(2) |
| NormL(2) && NotNormL(1) && LT_C_PauseT(2) && NotNoisy(2) && NotNoisy(1) | Funny(1),N(2) |
| NormL(2) && NotNormL(1) && ZNNT(1) && FusionT(1) && WideW(1) && Noisy(1) && NoL(1) | N(1),N(2) |
| NormL(2) && NotNormL(1) && OKT(2) && NoL(1) && NNT(2) | D(1),N(2) |
| NoL(2) && NoL(1) && GoodT(2-1) && GoodT(1) && NormW(2) && NormW(1) && SameCluster(2,1) && SmallPop(2) | N(1),N(2) |
| NoL(2) && NoL(1) && OKT(2) && Noisy(2) && NNoiseW(2) && ZNNT(2) | D(1),N(2) |
| Otherwise | Defer |
| THREE BEAT CASE | |
| OKT(3) | D(1),D(2),N(3) |
| EarlyT(3) | Defer |
| NormL(3) && NormL(2) && GoodT(3-2) | SetQ(1),N(2),N(3) |
| NormL(3) && NotNormL(2) && EarlyT(2-1) && RunT(2) && NotNormW(2) && NotNormW(3) | Defer |
| NormL(3) && NotNormL(2) && NotNormL(1) && EarlyT(1) && AbnormalRhythm && NotNoisy(1) && NotNoisy(2) && NotNoisy(3) && (EarlyT(2-1)\|\|(GoodT(2-1) && WideW(2))) && TwaveT(2-1) && DiffAreaSign(1,2) | PVC(1),D(2),N(3) |
| NormL(3) && NotNormL(2) && NotNormL(1) && EarlyT(1) && AbnormalRhythm && NotNoisy(1) && NotNoisy(2) && Not Noisy(3) && (EarlyT(2-1)\|\|(GoodT(2-1) && WideW(2))) && Otherwise | PVC(1),PVC(2), PVC(3) |
| NormL(3) && NotNormL(2) && NotNormL(1) && GoodT(3-2) && NormW(3) && FusionT(2-1) && WideW(2) && FusionT(1) && WideW(1) && (SlateT(1) && SlateT(2))\|\|(SearlyT(1) && SearlyT(2)) | SupV(1),D(2),N(3) |
| NormL(3) && NotNormL(2) && NotNormL(1) && GoodT(3-2) && NormW(3) && FusionT(2-1) && WideW(2) && FusionT(1) && WideW(1) && Otherwise | Fusion(1), |
| Otherwise | Defer |
| FOUR BEAT CASE | |
| OKT(4) | D(1),D(2),D(3). N(4) |
| NormL(4) && NormL(3) && GoodT(4-3) | SetQ(1),SetQ(2), N(3),N(4) |
| (NormL(4)\|\|GoodT(4-3) && NormW(4))) && FusionT(3-2) && WideW(3) && FusionT(2-1) && WideW(2) && Fusion(1) && WideW(1) && (SlateT(3) && SlateT(2) && StateT(1))\|\|SearlyT(3) && SearlyT(2) && SearlyT(1)) | N(1),N(2),N(3), N(4) |
| (NormL(4)\|\|(GoodT(4-3) && NormW(4))) && FusionT(3-2) && WideW(3) && FusionT(2-1) && WideW(2) && FusionT(1) && WideW(1)&& Not((SlateT(3) && SlateT(2)&& SlateT(1))\|\|(SearlyT(3) && SearlyT(2)&&Searly-T(1))) | F(1), F(2) F(3), N(4) |
| Otherwise | Defer |

TABLE 1-continued

| RULES | QRS COMPLEX LABELING |
|---|---|
| FIVE BEAT CASE | |
| AbnormalRhythm && GoodT(5-4) && NormW(5) && NormW(4) && EarlyT(3-2) && EarlyT(2-1) && EarlyT(1) && NotNoisy(5) && NotNoisy(4) && NotNoisy(3) && NotNoisy(2) && NotNoisy(1) | PVC(1),PVC(2), PVC(3),N(4) N(5) |
| NormL(5) && NormL(4) && GoodT(5-4) | SetQ(1), SetQ(2),SetQ(3) N(4),N(5) |
| Otherwise | Defer |

What is claimed is:

1. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said determining step comprises:

generating a plurality of scalar signals based on said at least one digital signal;

locating said time of occurrence of said possible QRS complex by detecting a peak value within at least one of said plurality of scalar signals; and determining said noise attribute within said at least one scalar signal within a noise time window about said time of occurrence according to said threshold crossing criteria.

2. The method of claim 1, wherein said step of determining a noise attribute according to said threshold crossing criteria comprises:

varying a candidate noise threshold from a first adaptively determined threshold to a second determined threshold, in threshold steps, wherein said second threshold is greater than said first threshold;

for each threshold step, determining a candidate noise attribute based on said candidate noise threshold and at least one of said plurality of scalar signals, said candidate noise attribute comprising one of not noisy and noisy;

declaring said noise attribute to be not noisy when said candidate noise attribute is not noisy; and declaring said noise attribute to be noisy when said candidate noise threshold has been varied from said first threshold to said second threshold and said candidate noise attribute is noisy at each previous threshold step.

3. The method of claim 1, wherein said step of extracting comprises identifying and removing a bad QRS complex prior to said plotting step.

4. The method of claim 1, wherein said identifying step comprises identifying one of said clusters having the largest population of said possible first QRS complexes as a normal cluster so as to designate each of said first QRS complexes located within said normal cluster as a normal QRS complex.

5. The method of claim 1, wherein said identifying step comprises labeling a first one of said clusters as said normal cluster, and labeling a second one of said clusters as a PVC cluster based on populations of said first and second clusters and a timing between QRS complexes in said first and second clusters.

6. The method of claim 1, wherein said step of identifying further comprises characterizing a normal QRS complex according to features characterizing said normal cluster.

7. The method of claim 1, wherein said labeling step further comprises labeling each of said plurality of possible second QRS complexes based on at least one of said noise attribute and an average normal QRS complex characterized according to features of said normal cluster.

8. The method of claim 1, wherein said labeling step comprises labeling each of said second QRS complex, the based on said N features of said each QRS complex, the timing of said each QRS complex, the QRS complexes located within said normal cluster and the cluster within which said each QRS complex is located.

9. The method of claim 1, wherein said labeling step comprises the steps of:

annotating each of said second QRS complexes according to a plurality of rules based on said N features of said each QRS complex, the timing of said each QRS complex, the QRS complexes located within said normal cluster and said one cluster within which said each QRS complex is located, said one cluster having a cluster label.

10. The method of claim 1, wherein said method further comprises the step of:

evaluating said labeled QRS complexes to produce a signal indicative of a character of a rhythm state within said at least one digital signal.

11. The method of claim 10, wherein said method further comprises the steps of:

displaying selected arrhythmic portions of said indicative signal.

12. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said extracting step further comprises filtering said at least one digital signal through a filter selected from a plurality of alternative filters according to said noise attribute.

13. The method of claim 12, wherein said extracting step further comprises:

determining a width threshold according to said filtered at least one digital signal and said threshold crossing criteria;

determining an onset time according to said filtered at least one digital signal and said width threshold;

determining an offset time according to said filtered at least one digital signal and said width threshold; and determining a QRS width according to said onset time and said offset time.

14. The method of claim 13, wherein said extracting step further comprises:

determining a QRS complex center according to said onset time, said offset time and said filtered at least one digital signal;

determining a plurality of pre-areas arranged in time before said center; and determining a plurality of post-areas arranged in time after said center.

15. The method of claim 14, wherein said plurality of pre-areas comprises a signed pre-area and an unsigned pre-area and said plurality of post-areas comprises a signed post-area and an unsigned post-area.

16. The method of claim 14, wherein said step of determining a QRS complex center determines said center so that one of said plurality of pre-areas has a magnitude equal to a magnitude of one of said plurality of post-areas.

17. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said step of extracting comprises identifying and removing a bad QRS complex prior to said plotting step, and said step of identifying a bad QRS complex comprises comparing against a predetermined number, a number of threshold crossings resulting from said threshold crossing criteria of said step of producing a value of a noise attribute when said noise attribute value is not noisy, and declaring the beat bad when said comparison indicates the number of threshold crossings is less than said predetermined number.

18. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said at least one cluster comprises a plurality of clusters, and wherein said identifying step further comprises merging a first cluster having a largest population of said plurality of clusters and a second cluster being within a predetermined distance from said first cluster within said N-dimensional space to produce at least one merged cluster.

19. The method of claim 18, wherein said at least one merged cluster comprises a plurality of merged clusters, and wherein said identifying step further comprises:

determining an average backwards coupling interval for each of a largest and a second largest cluster of said plurality of merged clusters;

declaring bigeminy based on populations of said largest and second largest merged clusters and coupling intervals of said largest and second largest merged clusters; and labeling said largest merged cluster as normal and said second largest merged cluster as PVC when bigeminy is declared.

20. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said step of identifying further comprises characterizing a normal QRS complex according to features characterizing said normal cluster, and said step of characterizing comprises initializing normal QRS complex morphology parameters.

21. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said step of identifying further comprises characterizing a normal QRS complex according to features characterizing said normal cluster, and said step of characterizing comprises initializing normal QRS complex timing parameters.

22. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said step of identifying further comprises determining normal QRS complex parameters bounds.

23. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said plurality of possible second QRS complexes comprise both QRS complexes and false QRS complexes which are not QRS complexes, said labeling step further comprises annotating at least one of said plurality of possible second QRS complexes according to a plurality of rules based on said normal cluster and said N features of a selected plurality of possible QRS complexes selected from said plurality of possible second QRS complexes, and said selected plurality of possible QRS complexes comprises at least one of said possible second QRS complexes having a time of occurrence later in time than the time of occurrence of said annotated at least one of said plurality of possible second QRS complexes.

24. A method for detecting arrhythmia in at least one digital signal produced from at least one analog ECG signal provided by an ECG system, the method comprising the steps of:

determining a noise attribute within said at least one digital signal based on a time of occurrence of a possible QRS complex according to a threshold crossing criteria, said noise attribute comprising one of not noisy and noisy;

extracting a number N of features from said at least one digital signal based on said time of occurrence and said noise attribute;

plotting in an N-dimensional feature space said possible QRS complex according to said extracted N features;

first group plotting each of a plurality of possible first QRS complexes by determining, extracting and plotting according to said determining step, extracting step and plotting step to produce at least one cluster from said plurality of possible first QRS complexes;

identifying a normal cluster based on said at least one cluster;

second group plotting each of a plurality of possible second QRS complexes by determining, extracting and plotting according to said determining step, extracting step and plotting step to perform at least one of adding possible QRS complexes to said at least one cluster, and producing at least one additional cluster; and labeling each of said plurality of possible second QRS complexes within said at least one digital signal based on said normal cluster and said N features extracted from each of said possible second QRS complexes;

wherein said step of labeling further comprises:

identifying said patient rhythm state from said plurality of possible second QRS complexes; and reinitializing cluster labels when said patient rhythm state is identified as bizarre for a period of time.

25. An arrhythmia detector for detecting arrhythmia in at least one digital signal produced from at least one analog ECG signal provided by an ECG system comprising a processor having an input circuit for receiving said at least one digital signal and including:

means for determining a noise attribute within said at least one digital signal based on a time of occurrence of a possible QRS complex according to a threshold crossing criteria, said noise attribute comprising one of not noisy and noisy;

means for extracting a number N of features from said at least one digital signal based on said time of occurrence and said noise attribute;

means for plotting in an N-dimensional feature space said possible QRS complex according to said extracted N features;

means for first group plotting each of a plurality of possible first QRS complexes by determining, extracting and plotting according to said means for determining, extracting and plotting to produce at least one cluster from said plurality of possible first QRS complexes;

means for identifying a normal cluster based on said at least one cluster;

means for second group plotting each of a plurality of possible second QRS complexes by determining, extracting and plotting according to said means for determining, extracting and plotting to perform at least one of adding possible QRS complexes to said at least one cluster, and producing at least one additional cluster; and means for labeling each of said plurality of possible second QRS complexes within said at least one digital signal based on said normal cluster and said N features extracted from each of said possible second QRS complexes;

wherein said means for determining further comprises:

means for generating a plurality of scalar signals based on said at least one digital signal, means for locating said time of occurrence of said possible QRS complex by detecting a peak value within said at least one scalar signal, and means for determining said noise attribute within said at least one scalar signal within a noise time window about said time of occurrence according to said threshold crossing criteria.

26. The arrhythmia detector of claim 25, wherein said means for extracting comprises means for identifying and removing a bad QRS complex prior to plotting by said means for plotting.

27. The arrhythmia detector of claim 25, wherein said means for labeling labels each of said plurality of possible second QRS complexes based on at least one of said noise attribute and an average normal QRS complex characterized according to features of said normal cluster.

28. The arrhythmia detector of claim 25, wherein said means for labeling labels each of said second QRS complexes based on said N features of said each QRS complex, the timing of said each QRS complex, the QRS complexes located within said normal cluster and the cluster within which said each QRS complex is located.

29. The arrhythmia detector of claim 25, wherein said means for labeling annotates each of said second QRS complexes according to a plurality of rules based on said N features of said each QRS complex, the timing of said each QRS complex, the QRS complexes located within said normal cluster and said one cluster within which said each QRS complex is located, said one cluster having a cluster label.

30. The arrhythmia detector of claim 25, wherein said detector further comprises:

means for evaluating said labeled QRS complexes to produce a signal indicative of a character of a rhythm state within said at least one digital signal.

31. The arrhythmia detector of claim 30, wherein said detector further comprises:

means for displaying selected arrhythmic portions of said indicative signal.

32. The arrhythmia detector of claim 28, wherein said means for determining a noise attribute according to said threshold crossing criteria comprises:

means for varying a candidate noise threshold from a first adaptively determined threshold to a second determined threshold, in threshold steps, wherein said second threshold is greater than said first threshold;

for each threshold step, said means for determining determines a candidate noise attribute based on said candidate noise threshold and one of said plurality of scalar signals, said candidate noise attribute comprising one of not noisy and noisy;

wherein said noise attribute is declared to be not noisy when said candidate noise attribute is not noisy; and wherein said noise attribute is declared to be noisy when said candidate noise threshold has been varied from said first threshold to said second threshold and said candidate noise attribute is noisy at each previous threshold step.

33. An arrhythmia detector for detecting arrhythmia in at least one digital signal produced from at least one analog ECG signal provided by an ECG system comprising a processor having an input circuit for receiving said at least one digital signal and including:

means for determining a noise attribute within said at least one digital signal based on a time of occurrence of a possible QRS complex according to a threshold crossing criteria, said noise attribute comprising one of not noisy and noisy;

means for extracting a number N of features from said at least one digital signal based on said time of occurrence and said noise attribute;

means for plotting in an N-dimensional feature space said possible QRS complex according to said extracted N features;

means for first group plotting each of a plurality of possible first QRS complexes by determining, extracting and plotting according to said means for determining, extracting and plotting to produce at least one cluster from said plurality of possible first QRS complexes;

means for identifying a normal cluster based on said at least one cluster;

means for second group plotting each of a plurality of possible second QRS complexes by determining, extracting and plotting according to said means for determining, extracting and plotting to perform at least one of adding possible QRS complexes to said at least one cluster, and producing at least one additional cluster; and means for labeling each of said plurality of possible second QRS complexes within said at least one digital signal based on said normal cluster and said N features extracted from each of said possible second QRS complexes;

wherein said means for extracting further comprises means for filtering said at least one digital signal through a filter selected from a plurality of alternative filters according to said noise attribute.

34. The arrhythmia detector of claim 33, wherein said means for extracting further comprises:

means for determining a width threshold according to said filtered at least one digital signal and said threshold crossing criteria;

means for determining an onset time according to said filtered at least one digital signal and said width threshold;

means for determining an offset time according to said filtered at least one digital signal and said width threshold; and means for determining a QRS width according to said onset time and said offset time.

35. The arrhythmia detector of claim 34, wherein said means for extracting further comprises:

means for determining a QRS complex center according to said onset time, said offset time and said filtered at least one digital signal;

means for determining a plurality of pre-areas arranged in time before said center; and means for determining a plurality of post-areas arranged in time after said center.

36. The arrhythmia detector of claim 35, wherein said plurality of pre-areas comprises a signed pre-area and an unsigned pre-area and said plurality of post-areas comprises a signed post-area and an unsigned post-area.

37. The arrhythmia detector of claim 35, wherein said means for determining a QRS complex center determines said center so that one of said plurality of pre-areas has a magnitude equal to a magnitude of one of said plurality of post-areas.

38. An arrhythmia detector for detecting arrhythmia in at least one digital signal produced from at least one analog ECG signal provided by an ECG system comprising a processor having an input circuit for receiving said at least one digital signal and including:

means for determining a noise attribute within said at least one digital signal based on a time of occurrence of a possible QRS complex according to a threshold crossing criteria, said noise attribute comprising one of not noisy and noisy;

means for extracting a number N of features from said at least one digital signal based on said time of occurrence and said noise attribute;

means for plotting in an N-dimensional feature space said possible QRS complex according to said extracted N features;

means for first group plotting each of a plurality of possible first QRS complexes by determining, extracting and plotting according to said means for determining, extracting and plotting to produce at least one cluster from said plurality of possible first QRS complexes;

means for identifying a normal cluster based on said at least one cluster;

means for second group plotting each of a plurality of possible second QRS complexes by determining, extracting and plotting according to said means for determining, extracting and plotting to perform at least one of adding possible QRS complexes to said at least one cluster, and producing at least one additional cluster; and means for labeling each of said plurality of possible second QRS complexes within said at least one digital signal based on said normal cluster and said N features extracted from each of said possible second QRS complexes;

wherein said means for extracting comprises means for identifying and removing a bad QRS complex prior to plotting by said means for plotting, and said means for identifying a bad QRS complex comprises means for comparing against a predetermined number, a number of threshold crossings resulting from said threshold crossing criteria of said means for producing a value of a noise attribute when said noise attribute value is not noisy, and means for declaring the beat bad when said comparison indicates the number of threshold crossings is less than said predetermined number.

39. An arrhythmia detector for detecting arrhythmia in at least one digital signal produced from at least one analog ECG signal provided by an ECG system comprising a processor having an input circuit for receiving said at least one digital signal and including:

means for determining a noise attribute within said at least one digital signal based on a time of occurrence of a possible QRS complex according to a threshold crossing criteria, said noise attribute comprising one of not noisy and noisy;

means for extracting a number N of features from said at least one digital signal based on said time of occurrence and said noise attribute;

means for plotting in an N-dimensional feature space said possible QRS complex according to said extracted N features;

means for first group plotting each of a plurality of possible first QRS complexes by determining, extracting and plotting according to said means for determining, extracting and plotting to produce at least one cluster from said plurality of possible first QRS complexes;

means for identifying a normal cluster based on said at least one cluster;

means for second group plotting each of a plurality of possible second QRS complexes by determining, extracting and plotting according to said means for determining, extracting and plotting to perform at least one of adding possible QRS complexes to said at least one cluster, and producing at least one additional cluster; and means for labeling each of said plurality of possible second QRS complexes within said at least one digital signal based on said normal cluster and said N features extracted from each of said possible second QRS complexes;

wherein said plurality of possible second QRS complexes comprise both QRS complexes and false QRS complexes which are not QRS complexes, said means for labeling annotates at least one of said plurality of possible second QRS complexes according to a plurality of rules based on said normal cluster and said N features of a selected plurality of possible QRS complexes selected from said plurality of possible second QRS complexes, and said selected plurality of possible QRS complexes comprises at least one of said possible second QRS complexes having a time of occurrence later in time than the time of occurrence of said annotated at least one of said plurality of possible second QRS complexes.

* * * * *